(12) United States Patent
Kimmel

(10) Patent No.: US 8,617,128 B2
(45) Date of Patent: Dec. 31, 2013

(54) LABELING OF MEDICAL DEVICES

(75) Inventor: Michael W. Kimmel, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/396,857

(22) Filed: Feb. 15, 2012

(65) Prior Publication Data

US 2013/0211346 A1     Aug. 15, 2013

(51) Int. Cl.
*A61M 25/00*     (2006.01)
(52) U.S. Cl.
USPC ........................................................ 604/264
(58) Field of Classification Search
USPC ........................................................ 604/264
See application file for complete search history.

(56) References Cited

U.S. PATENT DOCUMENTS

| | | | |
|---|---|---|---|
| 4,572,605 A | 2/1986 | Hess | |
| 5,967,988 A * | 10/1999 | Briscoe et al. | 600/458 |
| 6,026,567 A | 2/2000 | Swoyer et al. | |
| 6,144,011 A | 11/2000 | Moss et al. | |
| 7,541,088 B2 * | 6/2009 | Bennett et al. | 428/216 |
| 7,972,312 B2 * | 7/2011 | Koopman | 604/187 |
| 2002/0067900 A1 * | 6/2002 | Mills et al. | 385/114 |
| 2003/0195473 A1 * | 10/2003 | Hetzler et al. | 604/181 |
| 2004/0253185 A1 * | 12/2004 | Herweck et al. | 424/10.2 |
| 2007/0179461 A1 | 8/2007 | Sambasivam et al. | |
| 2009/0131910 A1 * | 5/2009 | Webler | 604/523 |
| 2010/0130962 A1 * | 5/2010 | Ebert et al. | 604/529 |

FOREIGN PATENT DOCUMENTS

EP     1 659 162 A1     5/2006

OTHER PUBLICATIONS (PCT/US2013/024885) PCT Notification of Transmittal of the International Search Report and the Written Opinion of the International Searching Authority.

* cited by examiner

*Primary Examiner* — Nicholas Lucchesi
*Assistant Examiner* — Rebecca E Eisenberg
(74) *Attorney, Agent, or Firm* — Reed A. Duthler

(57) ABSTRACT

An interventional medical device, for example, a chronic implantable medical electrical lead or drug delivery catheter, or an acute medical therapy delivery and/or diagnostic tool, such as a guide catheter, includes a label formed by laser marking a $TiO_2$-loaded silicone medical adhesive, which is primarily employed for filling and bonding in the device. A laser marking apparatus is employed to form marks of the label in the cured adhesive that forms a backfill and bond in the device.

5 Claims, 4 Drawing Sheets

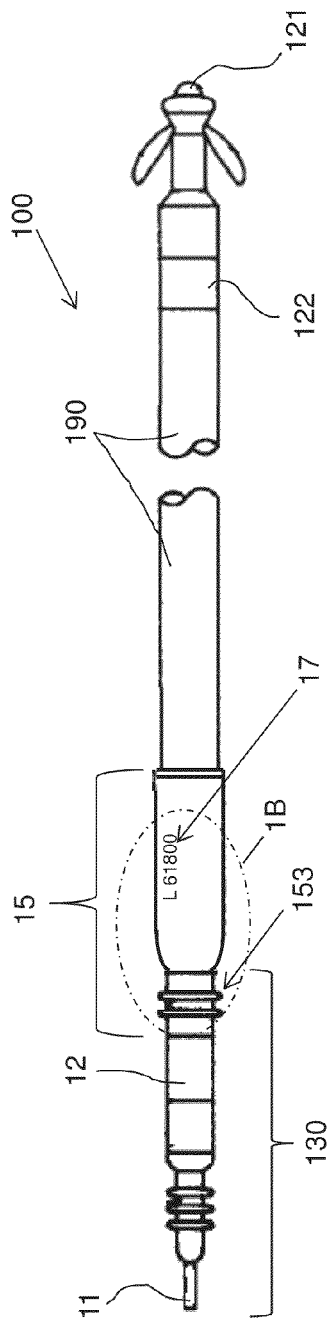
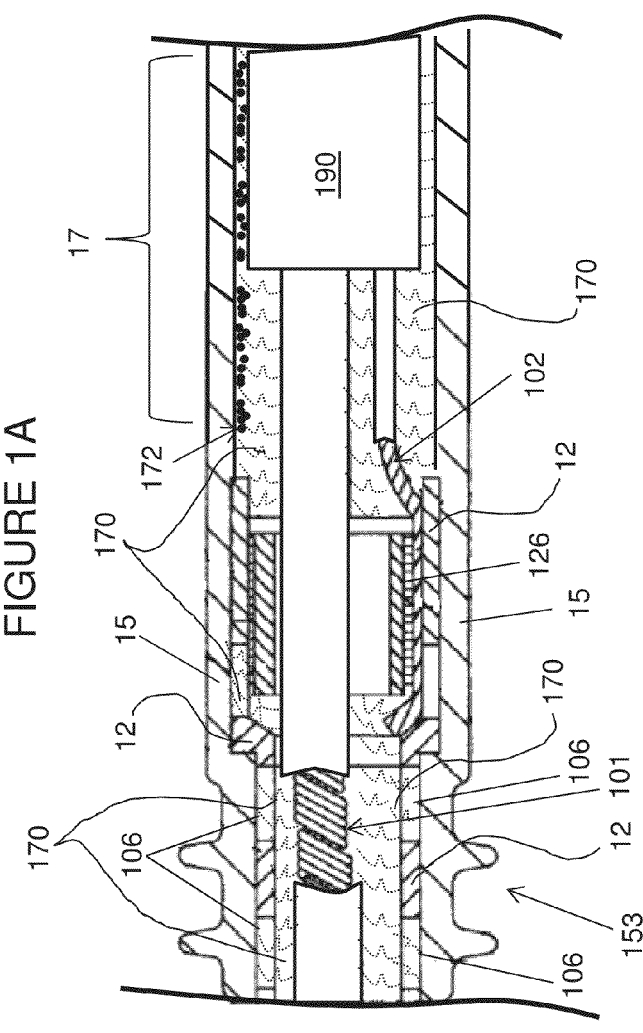
FIGURE 1A
FIGURE 1B

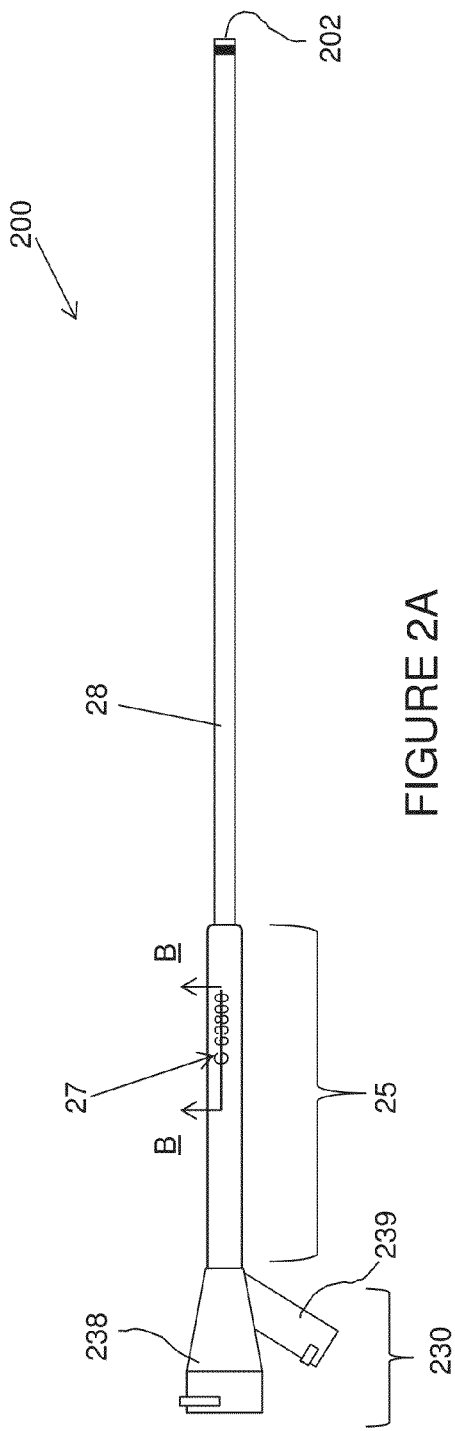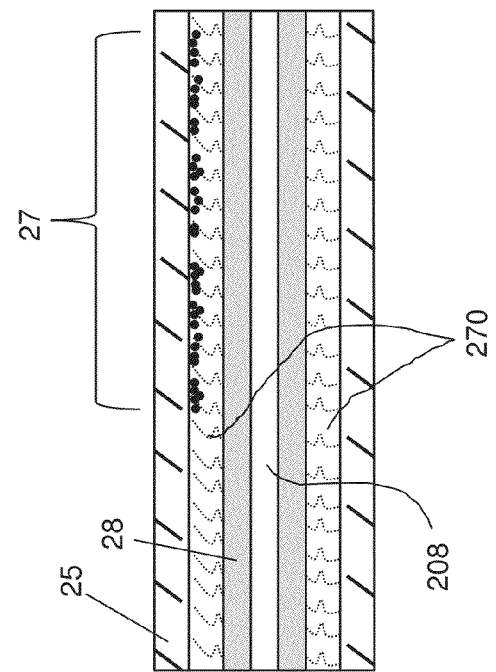

LABELING OF MEDICAL DEVICES

FIELD OF THE DISCLOSURE

The present invention pertains to medical devices and more particularly to the labeling thereof.

BACKGROUND

Labeling of medical devices is often necessary, both to enable the manufacturers of the devices to meet the requirements for device tracking (i.e. via serial numbering) and to enable customers in the clinical setting to identify and properly employ the devices (i.e. via a model number and/or functional identification of parts). A label for an interventional medical device may be formed as a separate component, for example, being printed on relatively thin biocompatible film (i.e. polyester, polyolefin or fluoropolymer), that is assembled into the device; alternately, a label can be formed on another device component, the primary function of which is independent of that of labeling, for example, by printing, etching or molding marks of the label directly thereon. In either case it is desirable for the label to be readily visible and legible without increasing an overall bulk of the interventional medical device or adversely impacting the function or handling of the device. Although a variety of labeling methods are known in the art, there is still a need for new types of labeling in the medical device industry.

SUMMARY

Embodiments and methods of the present invention pertain to effectively labeling interventional medical devices without the need for dedicated label components and without compromising device performance and/or handling. Embodiments of the present invention include, for example, chronically implantable medical electrical leads, chronically implantable drug delivery catheters, and acute medical therapy delivery and/or diagnostic tools such as guide catheters, wherein labels are formed by laser marking a silicone medical adhesive, which is loaded with titanium dioxide ($TiO_2$), and is preferably primarily employed for filling and bonding in the device. According to methods of the present invention, an ultraviolet laser beam of a laser marking apparatus is employed to form marks of the label in the cured silicone medical adhesive that preferably forms a backfill and bond of the device.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 1A is a plan view of an exemplary medical electrical lead;

FIG. 1B is a partial cut-away section of a portion of the lead of FIG. 1A, according to some embodiments of the present invention;

FIG. 2A is a plan view of an exemplary catheter;

FIG. 2B is a cross-section view through section line B-B of FIG. 2A, according to some alternate embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 3:
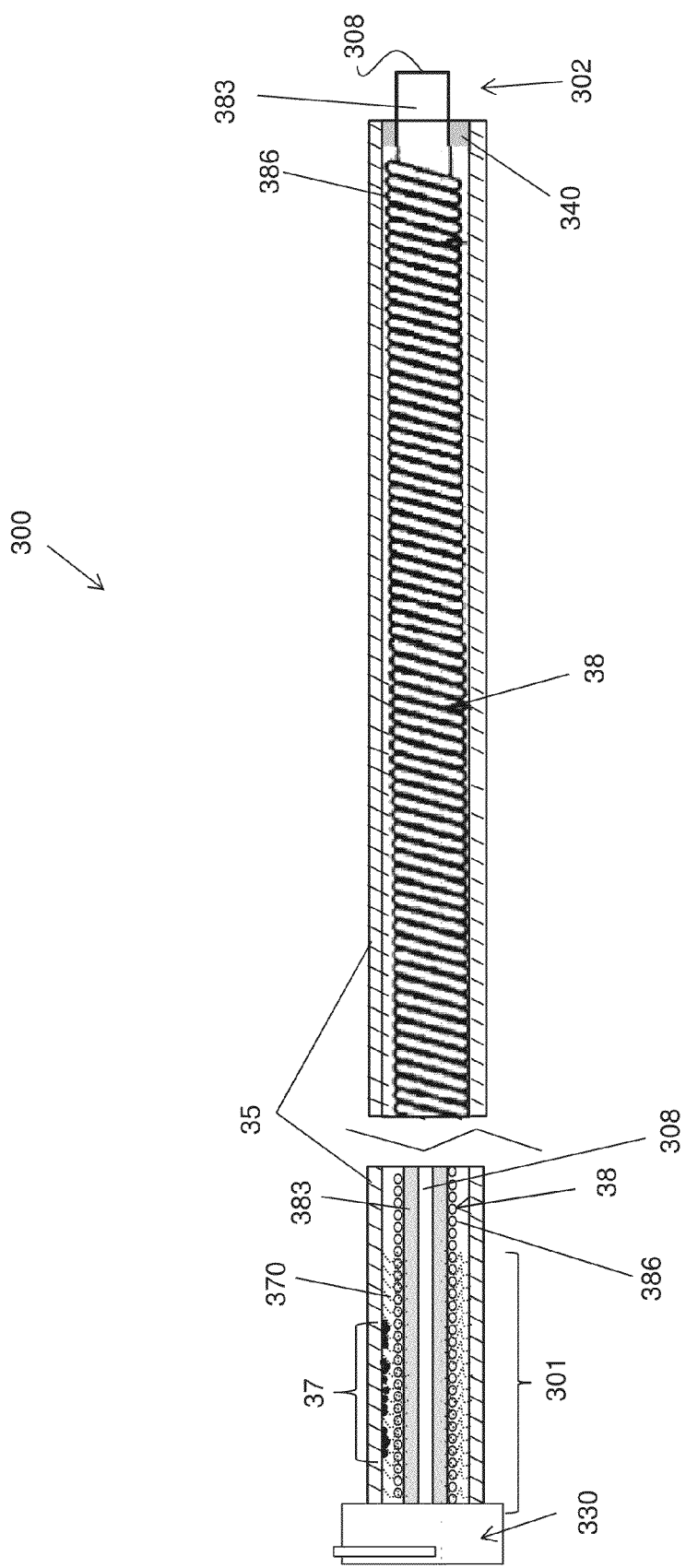
FIG. 3 is a plan view with cut-away section views of an implantable drug delivery catheter, according to some embodiments.

FIGS. 1A, 2A and 3 are plan views of three examples of interventional medical devices including respective labels 17, 27, 37, according to some embodiments of the present invention. FIG. 1A illustrates an implantable medical electrical lead 100, for example, that may be employed to sense cardiac depolarization signals and deliver pacing pulses via electrodes 121 and 122; FIG. 2A illustrates a guide catheter 200, for example, that may be employed to deliver a diagnostic or therapeutic device or agent through a lumen 208 (FIG. 2B) thereof; and FIG. 3 illustrates a chronically implantable drug delivery catheter 300. Section views in FIGS. 1B, 2B and 3 show portions of each device 100, 200, 300 in which the corresponding label 17, 27, 37 is formed; and, with further reference to FIGS. 1A, 2A and 3, the portion that contains each label 17, 27, 37 is preferably located in proximity to a connector member 130, 230, 330 of the corresponding device 100, 200, 300. However, it should be noted that the location of labels, according to alternate embodiments, may be elsewhere. Furthermore, other types interventional medical devices, such as implantable sensors and hydrocephalus shunts, may include one or more labels formed according to embodiments of the invention described below.

With further reference to FIGS. 1A-B, connector member 130 includes a first contact 11 and a second contact 12 configured for electrical coupling to corresponding electrical contacts within a port of a connector module of an implantable medical device (not shown), for example, as dictated by what is known as the IS-1 industry standard. FIGS. 1A-B illustrate label 17 located between an outer sleeve 15 and an inner assembly of lead 100; outer sleeve 15 includes a set of sealing rings 153, which is one of two sets employed by connector member 130 to provide electrical isolation for contacts 11, 12 within the aforementioned port of the device connector module. FIG. 1B further illustrates inner assembly including components of connector member 130, in particular, a portion of contact 12 and a swaging core 126, proximal portions of first and second conductors 101, 102, and a proximal portion of an elongate insulative body 190. According to the illustrated embodiment, first contact 11 is coupled to electrode 121 by first elongate conductor 101, and second contact 12, is coupled to electrode 122 by second elongate conductor 102; each of conductors 101, 102 extend, between the corresponding electrode and contact, within individual lumens of insulative body 190, for example, formed from a multi-lumen tubing made from medical grade silicone rubber, according to fabrication methods known in the art. The junctions between each of conductors 101, 102 and the corresponding contacts 11, 12 and electrodes 121, 122 may be formed according to any suitable method known in the art.

With further reference to FIG. 1B, outer sleeve 15 is shown overlaying the above-described inner assembly of lead 100 with a $TiO_2$-loaded silicone medical adhesive 170 filling a gap between sleeve 15 and the inner assembly. In particular, FIG. 1B illustrates medical adhesive 170 extending within second contact 12 and through cross bores 106 thereof and around conductors 101, 102 and the junction of conductor 102 with contact 12 (formed between an inner surface of contact 12 and a swaging core 126), and around the proximal portion of lead body 190, for the purpose of both filling gaps and bonding outer sleeve 15 to the inner assembly. Loading adhesive 170 with the $TiO_2$ changes the appearance thereof from transparent and colorless to opaque and white. Commonly assigned U.S. Pat. No. 6,026,567 includes a more detailed description of a junction for a connector assembly that is similar to that illustrated between conductor 102 and contact 12, as well as a general description of backfilling with silicone medical adhesive to interconnect a sleeve, similar to sleeve 15, to underlying components. A connector assembly, which is similar to that described in the '567 patent and which includes $TiO_2$-loaded silicone medical adhesive filled through cross bores of a connector component similar to second contact 12, has been employed in commercially available implantable medical electrical leads distributed by Medtronic, Inc. However, the illustrated embodiment of the present invention employs $TiO_2$-loaded silicone medical adhesive 170 distal to contact 12, such that the backfill of adhesive 170 extends the bond between sleeve 15 and the inner assembly along a length that is distal to contact 12, provides an adequate area for label 17, and further provides, in conjunction with sleeve 15, strain relief for the junction between the inner assembly and connector member 130 (i.e. the press-fit junction of conductor 102 between swaging core 126 and second contact 12). Furthermore, according to embodiments of the present invention, label 17 is formed directly in $TiO_2$-loaded silicone medical adhesive 170, after adhesive 170 cures to form a bond between outer sleeve 15 and inner assembly. Label 17 is formed by an ultraviolet (UV) laser beam, which changes a portion 172 of adhesive 170, which is immediately adjacent inner surface of sleeve 15, from white to a blackish color, while a remainder of adhesive 170 remains white, as will be described in greater detail below. The loading of $TiO_2$ in adhesive 170 can be at least 1-2% or up to approximately 40%, by weight.

FIGS. 2A-B illustrate guide catheter 200 including an outer sleeve 25 surrounding an inner assembly, which is formed by a proximal portion of an elongate tubular member 28 that defines lumen 208. FIG. 2A further illustrates tubular member 28 extending distally from sleeve 25 to a distal opening 202 of lumen 208, and connector member 230 of catheter 200, which is joined to a proximal end of tubular member 28, including a hub 238 and side port arm 239, each of which provide proximal openings into lumen 208 and have luer connector fittings formed thereon for connection with fluid sources (i.e. syringe) and/or valve members (i.e. stopcock or Toughy-Borst). With further reference to FIGS. 2A-B, label 27 of catheter 200 is likewise formed directly in a $TiO_2$-loaded silicone medical adhesive 270 that forms a backfill and bond between outer sleeve 25 and tubular member 28. According to some embodiments, sleeve 25 in conjunction with adhesive 270 further provides strain relief for the junction between tubular member 28 and connector member 230.

FIG. 3 illustrates drug delivery catheter 300 including an outer sleeve 35 surrounding an inner assembly 38, which includes an elongate inner tubing 383 and an elongate coil 386. According to the illustrated embodiment, inner tubing 383 defines a lumen 308, through which a therapeutic agent is delivered, for example, from a pump and corresponding reservoir, to which catheter 300 is connected by connector member 330, to a site in proximity to a distal end of catheter 300; and coil 38, in combination with outer sleeve 35, provides strain relief for inner tubing 383 along a majority of a length thereof. FIG. 3 further illustrates an adhesive bond 340 (i.e. silicone medical adhesive) between outer sleeve 35 and inner tubing 383, in proximity to distal end 302 of catheter 300, and a backfill of $TiO_2$-loaded silicone medical adhesive 370 located between sleeve 35 and inner assembly 38, along a proximal portion 301 of catheter 300, for example, to bond outer sleeve 35 and connector member 330 to inner assembly 38 and to fill the gap therebetween and provide additional strain relief adjacent to connector member 330. Like the above-described embodiments, label 37 is formed directly in $TiO_2$-loaded silicone medical adhesive 370 by an ultraviolet (UV) laser beam, which changes a portion of adhesive 370, which is immediately adjacent inner surface of sleeve 35, from white to a blackish color, while a remainder of adhesive 370 remains white, as will be described in greater detail below. The loading of $TiO_2$ in adhesive 370 can be at least 1-2% or up to approximately 40%, by weight.

According to exemplary embodiments, each of outer sleeves 15, 25, 35 is preferably formed from medical grade silicone rubber, which has a wall thickness, over the area corresponding to label 17, 27, 37 of between approximately 0.003 inch and approximately 0.01 inch; and a size of the gap between the inner surface of outer sleeve 15, 25 and the corresponding inner assembly, which is filled by the adhesive and includes the label, may be between approximately 0.002 inch and approximately 0.01 inch. Silicone rubber is transparent for the viewing of the corresponding label 17, 27 therethrough, as well as for the transmission of UV radiation therethrough to form the corresponding label 17, 27, 37, as described below. Those skilled in the art will appreciate that any of sleeves 15, 25, 35 may be formed from any other suitable UV-transparent and biocompatible material, for example, polyurethane.

Figure 4:
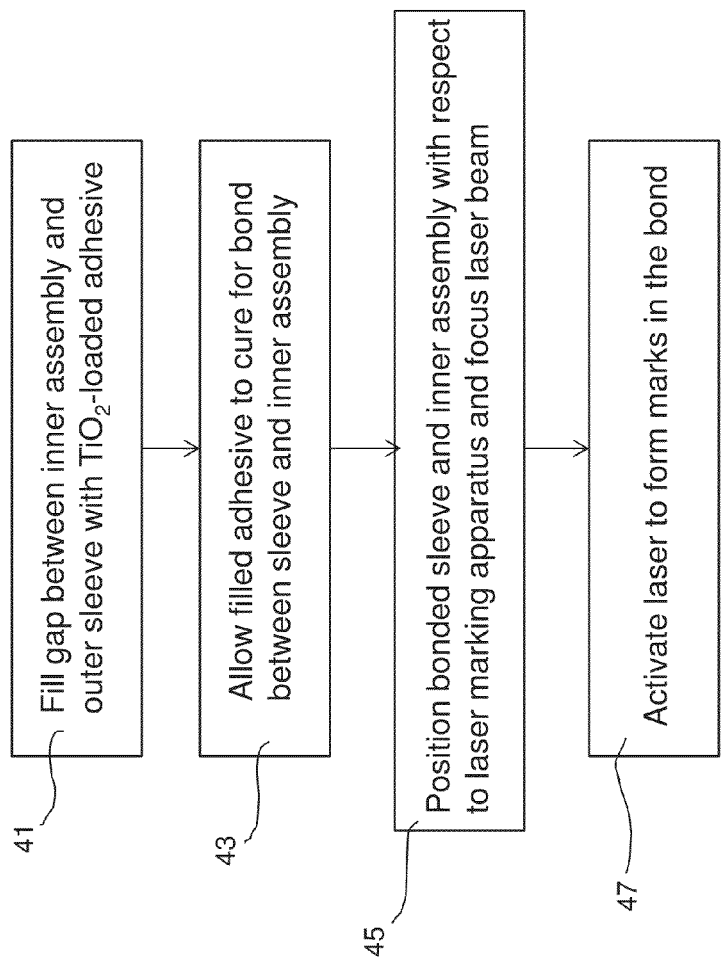
FIG. 4 is a flow chart outlining some methods of the present invention.

FIG. 4 is a flow chart outlining some methods of the present invention. In an initial step 41, the gap between the inner assembly and the outer sleeve is filled with the $TiO_2$-loaded silicone medical adhesive. For the above described exemplary embodiments, joining the inner assembly to the connector member may precede or follow step 41, wherein the filling may be accomplished as the sleeve is moved into position around the inner assembly, or just after moving the sleeve into position. After the filled $TiO_2$-loaded silicone medical adhesive is allowed to cure, per step 43, according to any suitable process known in the art, the bonded sleeve and inner assembly is positioned with respect to a laser marking apparatus so that an UV laser beam thereof may be directed toward the bond and then focused to a depth, which is approximately at the interface between the inner surface of the sleeve and the $TiO_2$-loaded silicone medical adhesive, per step 45. Once the laser beam is focused, the marking apparatus is activated, per step 47, to form marks of a predetermined label in the bond, for example, by a mask imaging technique or a scanning spot technique known in the art. Multiple assemblies of outer sleeves bonded to inner assemblies may be loaded into an automated rotary fixture for successive positioning, focusing and forming of marks according to steps 45 and 47. In addition, the fixture may be adapted to rotate each individual assembly for steps 45 and 47 so that marks in the bond can be formed in multiple locations about a circumference of the bond.

The UV laser beam changes the color of the $TiO_2$ particles in the loaded adhesive from white to a blackish color by rearranging the crystalline structure thereof on a microscopic scale, for example, to a depth of approximately 20 micron (0.0008 inch). The laser marking apparatus employed by methods of the present invention may be any suitable apparatus known in the art, for example, the Violino UV™ Nd:YVO4 Laser source used with a scanning head for micro marking (Laservall North America). Additional exemplary apparatus are described in U.S. Pat. No. 6,144,011, which is hereby incorporated by reference.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical device comprising an inner assembly, an outer sleeve, and a label, the label being located between the inner assembly and the outer sleeve and visible, through the outer sleeve, to the naked eye, and the label comprising:
   a titanium dioxide-loaded silicone medical adhesive, the adhesive filling a gap between the outer sleeve and the inner assembly and bonding the outer sleeve to the inner assembly; and
   wherein the titanium dioxide-loaded silicone medical adhesive includes a portion that is a different color from a remainder thereof, the portion being located immediately adjacent an inner surface of the bonded outer sleeve.

2. The device of claim 1, wherein:
   the inner assembly comprises an elongate conductor and a connector contact coupled thereto; and
   the outer sleeve comprises sealing rings formed along an outer surface thereof, the sealing rings being located in proximity to the connector contact surface.

3. The device of claim 1, wherein:
   the inner assembly comprises a tubular member extending from a proximal end thereof to a distal end thereof over a first length; and
   the outer sleeve extends around the tubular member over a second length, the second length being less than the first length.

4. The device of claim 3, further comprising a connector member joined to a proximal end of the tubular member; and wherein the tubular member defines a lumen through which a therapeutic agent is delivered from a pump and corresponding reservoir, connected to the device by the connector member, to a site in proximity to a distal end of the device.

5. The device of claim 1, further comprising a connector member joined to a proximal end of the inner assembly; and wherein the outer sleeve and the medical adhesive together provide strain relief for the junction between the connector member and the inner assembly.

* * * * *